United States Patent [19]

Ahond et al.

[11] Patent Number: 4,801,602
[45] Date of Patent: Jan. 31, 1989

[54] NEW BIOLOGICALLY ACTIVE SUBSTANCE CALLED GIROLLINE, EXTRACTED FROM THE SPONGE PSEUDAXINYSSA CANTHARELLA PROCESS FOR ITS PREPARATION AND PHARMACEUTICAL COMPOSITIONS CONTAINING IT

[75] Inventors: Alain Ahond, Malakoff; Pierre Laboute; Dominique Laurent, both of Noumea; Pierre Potier, Bois D'Arcy; Christiane Poupat, Plaisir; Jacques Pusset; Michele Pusset, both of Saint-Yon; Odile Thoison, Morangis, all of France

[73] Assignee: Rhone-Poulenc Sante, Courbevoie, France

[21] Appl. No.: 102,765

[22] Filed: Sep. 24, 1987

Related U.S. Application Data

[63] Continuation of Ser. No. 886,037, Jul. 16, 1986, abandoned.

[30] Foreign Application Priority Data

Jul. 18, 1985 [FR] France ................... 85 10997

[51] Int. Cl.⁴ ................... A61K 31/415; C07D 233/64
[52] U.S. Cl. ................... 514/398; 424/195.1; 548/337
[58] Field of Search ................... 424/195.1; 548/337; 514/398

[56] References Cited

U.S. PATENT DOCUMENTS 3,804,850  4/1974  Martin et al. ................... 548/337

FOREIGN PATENT DOCUMENTS 0066909  12/1982  European Pat. Off. ............ 514/398

OTHER PUBLICATIONS

Cancer Treatment Reports, vol. 62, No. 10, Oct. 1978, pp. 1471–1488, Corbett, et al.
Cancer Chemotherapy Reports Part 2, vol. 5, No. 1, Dec. 1975, pp. 89–109, Martin, et al.
Cancer Research, 41, pp. 1271–1280, Apr. 1981, Talmadge et al.
Eur J Cancer Clin Oncol. vol. 20, No. 5, pp. 699–705, 1984, Langdon, et al.
Physiological Review, vol. 52, No. 3, Jul. 1972, Potter, pp. 631–646 and 648 to 719.
Proc. Natl. Acad. Sci. USA vol. 80, pp. 1073–1077, Feb. 1983, Mushinski et al.
Levi; Bull. Mus. Natn. His. Nat. Poris, 4th series, 5, pp. 719–722 (1983).
Goldin, et al.; "Historical Development and Current Strategy of the Methods of Cancer Institute Drug Development Program", Methods in Cancer Research, vol. XVI, pp. 165–245 (1979).
Merck Index for Daunorubicin (9th Ed), p. 371, #2815 (no date).

*Primary Examiner*—Joseph Paul Brust
*Attorney, Agent, or Firm*—Stevens, Davis, Miller & Mosher

[57] ABSTRACT

The substance of formula:

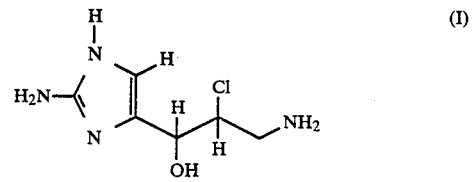

called girolline, which is new, can be extracted from the *Pseudaxinyssa cantharella* sponge. It has remarkable antitumour properties.

4 Claims, No Drawings

NEW BIOLOGICALLY ACTIVE SUBSTANCE CALLED GIROLLINE, EXTRACTED FROM THE SPONGE PSEUDAXINYSSA CANTHARELLA PROCESS FOR ITS PREPARATION AND PHARMACEUTICAL COMPOSITIONS CONTAINING IT

This application is a continuation of application Ser. No. 886,037, filed July 16, 1986 and now abandoned.

The present invention relates to biologically active substances, their preparation and compositions containing them.

The new substance, called girolline, is extracted from the sponge *Pseudaxinyssa cantharella*, the characteristics of which have been described by C. Levi, Bull. Mus. Natn. Hist. Nat. Paris, 4th series, 5, 719–722 (1983) and which may be fished in the Nouméa Lagoon (New Caledonia).

Girolline forms a very hygroscopic white powder. Its structure, in the form of a base or a salt, may be presented by the following formulae:

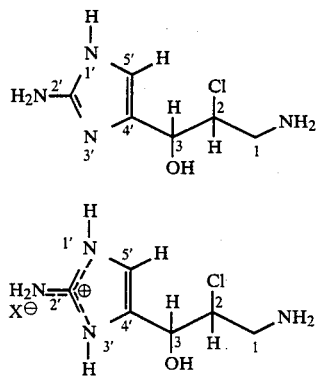

in which $X^{\ominus}$ represents an anion such as the chloride anion ($Cl^-$).

The structure of girolline has been determined from its nuclear magnetic resonance spectra ($^1H$, $^{13}C$, $^{15}N$) and mass spectrum and the spectra of its derivatives.

The structure of the hydrocarbon chain has been determined by the nuclear magnetic resonance spectra ($^1H$ and $^{13}C$) of girolline (400 and 100.1 MHz, dissolved in $D_2O$ with, as the external reference, dioxan-TMS for $^{13}C$ and $D_2O$ 4.83 ppm for $^1H$) which give the following characteristics:

| | |
|---|---|
| —C(1)-H$_2$ | $\delta_C$ = 44.40 ppm (t, J = 147 Hz) <br> $\delta_H$ = 3.48 ppm (dd, J = 13.7 and 9.4 Hz) and 3.63 ppm (dd, J = 13.7 and 3.3 Hz) |
| —C(2)-H | $\delta_C$ = 61.2 ppm (dd, J = 154 and 4 Hz) <br> $\delta_H$ = 4.62 ppm (dt, J = 9.4 and 3.3 Hz) |
| —C(3)-H | $\delta_C$ = 67.3 ppm (d, J = 146 Hz) <br> $\delta_H$ = 5.19 ppm (dd, J = 3.3 and 1 Hz) |
| =C(5')-H | $\delta_C$ = 113.25 ppm (d, J = 202 Hz) <br> $\delta_H$ = 6.80 ppm (d, J = 1 Hz) |
| =C(4') | $\delta_C$ = 126.25 ppm (d broadened, J = 6 Hz) |
| =C(2') | $\delta_C$ = 148.03 ppm (d broadened, J = 7 Hz) |

The $^{15}N$ nuclear magnetic resonance spectrum (40 MHz, dissolved in $D_2O$) gives three signals at 47.6; 71.4 and 151.3 ppm.

The mass spectrum of girolline makes it possible to confirm the presence of a chlorine atom linked to the skeleton:

D.C.I. (Desorption Chemical Ionization) ($NH_3$)→191 and 193: presence of one Cl(C)

D.C.I. (ND)→198: presence of 6 interchangeable H

F.A.B. (Fast Atomic Bombardment) (Xe)→191 and dimer at 381.

The derivatives which enabled the presence of oxygen to be confirmed were prepared in the following manner:

1. "Adamantyl" derivatives.

A solution of 15 mg (0.08 mmole) of girolline in 5 cc of water is brought to a pH of 8–9 by adding a 10% sodium bicarbonate solution. 0.24 mmole of adamantyl fluoroformate is then added, in 3 additions, dissolved in dioxan (3×0.3 cc). After 6 hours at a temperature of about 20°–23° C., the reaction mixture is extracted with ethyl ether. The organic extracts are purified by thick layer chromatography (silica; 1:1 methylene chloride-/ethyl acetate by volume). Two products are thus isolated:

(a) a less polar product (7.3 mg) of which the characteristics are as follows:

Rf=0.81

$[\alpha]_D$= +12.6 (C=3.1; chloroform)

mass spectrum: F.A.B.→725 and 727 (isotope Cl)

proton nuclear magnetic resonance spectrum (200 MHz, dissolved in $CDCl_3$):

| | |
|---|---|
| adamantyl | $\delta_H$ = 1.70 and 2.25 ppm (2m) |
| —C(1)-H$_2$ | $\delta_H$ = 3.48 ppm (m) |
| —C(2)-H | $\delta_H$ = 4.47 ppm (m) |
| —C(3)-H | $\delta_H$ = 5.67 ppm (d, J = 6 Hz) |
| =C(5')-H | $\delta_H$ = 6.96 ppm (s) |
| —N—H | $\delta_H$ = 5.30 and 5.87 ppm (m from 1H and 2H) |

A study of this spectrum shows that the product obtained is trisubstituted.

(b) A more polar product (9 mg) of which the characteristics are as follows:
Rf=0.27
mass spectrum: F.A.B.→547 and 549 (isotope Cl) proton nuclear magnetic resonance spectrum (200 MHz, dissolved in CDCl₃):

| adamantyl | $\delta_H$ = 1.67 and 2.18 ppm (2m) |
|---|---|
|  | $\delta_H$ = 3.40 and 3.73 ppm (2m) |
| —C(1)-H₂ |  |
| —C(2)-H | $\delta_H$ = 4.37 ppm (m) |
| —C(3)-H | $\delta_H$ = 4.77 ppm (d, J = 2 Hz) |
| =C(5')-H | $\delta_H$ = 6.96 ppm (s) |
| —N—H and —O—H | $\delta_H$ = 4.46; 5.50 and 5.90 ppm (3m) |

A study of this spectrum shows that the product obtained is disubstituted.

Between the two derivatives obtained, there is a difference $\Delta\delta_H$=1.10 ppm for —C(3)—H, from which it may be concluded that there is a hydroxyl radical in position 3—.

2. "acetylated" derivatives

The more polar "adamantyl" derivative is acetylated as follows: 0.55 cc of acetic anhydride is added to 10 mg of the more polar (M547-549) product in 0.6 cc of anhydrous pyridine. The mixture is shaken for 2 hours at a temperature of about 20° C. The reaction mixture is poured into iced water and then extracted with methylene chloride.

After evaporating the solvent, the crude product obtained is purified by thick layer chromatography (silica; 1:1 methylene chloride/ethyl acetate by volume). Two products are thus isolated:

(a) a di(O,N)-acetylated derivative of which the characteristics are as follows:
Rf=0.63
mass spectrum: c.i.→(Chemical Ionization)—631 and 633 (isotope Cl) proton nuclear resonance spectrum (200 MHz, dissolved in CDCl₃):

| adamantyl | $\delta_H$ = 1.65 and 2.18 ppm (2m) |
|---|---|
| —CO—CH₃ | $\delta_H$ = 2.28 and 2.47 ppm (2s) |
| —C(1)-H₂ | $\delta_H$ = 3.5 ppm (m) |
| —C(2)-H | $\delta_H$ = 4.55 ppm (d broadened, J = 6 Hz) |
| —C(3)-H | $\delta_H$ = 6.0 ppm (d, J = 6 Hz) |
| =C(5')-H | $\delta_H$ = 7.10 ppm (s) |
| —N—H | $\delta_H$ = 5.20 and 9.65 ppm (m) |

(b) a mono(O)-acetylated derivative of which the characteristics are as follows:
Rf=0.60
mass spectrum: c.i.→589 and 591 (isotope Cl) proton nuclear magnetic resonance spectrum (200 MHz, dissolved in CDCl₃):

| adamantyl | $\delta_H$ = 1.60 and 2.17 ppm (2m) |
|---|---|
| CO—C—H₃ | $\delta_H$ = 2.25 ppm (s) |
| —C(1)-H₂ | $\delta_H$ = 3.43 ppm (m) |
| —C(2)-H | $\delta_H$ = 4.47 ppm (m) |
| —C(3)-H | $\delta_H$ = 5.85 ppm (d, J = 6 Hz) |
| =C(5')-H | $\delta_H$ = 6.92 ppm (s) |
| —N—H | $\delta_H$ = 5.15 and 5.77 ppm. |

Between the monoacetylated derivative and the more polar non acetylated adamantyl derivative, there is a difference $\Delta\delta_H$=1.08 ppm for —C(3)—H, from which the presence of a hydroxyl radical in position 3-may be confirmed.

3. Dinitrophenyl derivative (a) bis(2,4-dinitrophenyl) derivative:

28 mg of sodium bicarbonate dissolved in 0.5 cc of distilled water are added to 14 mg (0.07 mmole) of girolline. After shaking for 30 minutes at ambient temperature, a solution of 112 mg of 2,4-dinitro-1-fluorobenzene in 2 cc of ethanol is added. The mixture is shaken for 2 hours at a temperature in the vicinity of 20° C. After concentrating to dryness, the residue is taken up with 20 cc of a methylene chloride/methanol mixture (8:2 by volume). After filtering through sintered glass and evaporating the filtrate to dryness, the residue (102 mg) is purified by flash-chromatography (Merck 7734 silica; column height 150 mm; diameter: 20 mm; pressure 0.3 bar; eluant: methylene chloride/methanol 8:2 by volume). The "bis(2,4-dinitrophenyl)" derivative (15 mg) is thus obtained, the characteristics of which are as follows:

Rf=0.23

[a]$_D$=0 (methanol)

mass spectrum: F.A.B.→523 and 525 (isotope Cl)

proton magnetic resonance spectrun (400 MHz, dissolved in CD4O):

| | |
|---|---|
| —C(1)-H: | $\delta_H$ = 3.86 ppm (dd, J = 15 and 7 Hz) |
| —C(1)—H: | $\delta_H$ = 4.0 ppm (dd, J = 15 and 5 Hz) |
| —C(2)-H: | $\delta_H$ = 4.55 ppm (m) |
| —C(3)-H: | $\delta_H$ = 4.80 ppm (d, J = 5 Hz) |
| =C(5')-H: | $\delta_H$ = 6.83 ppm (s) |

The protons of the phenyl rings are marked "or"

| | |
|---|---|
| =C(6''')-H | $\delta_H$ = 7.23 ppm (d, J = 9 Hz) |
| =C(6'')-H | $\delta_H$ = 7.97 ppm (d, J = 9 Hz) |
| =C(5''')-H | $\delta_H$ = 8.35 ppm (dd, J = 9 and 3 Hz) |
| =C(5'')-H | $\delta_H$ = 8.70 ppm (dd, J =9 and 2.5 Hz) |
| =C(3''')-H | $\delta_H$ = 8.98 ppm (d, J = 3 Hz) |
| =C(3'')-H | $\delta_H$ = 9.08 ppm (d, J = 2.5 Hz) |

(b) Acetylated "bis(2,4-dinitrophenyl)" derivative 9 mg of the "diphenyl" product are dissolved in 2 cc of acetic anhydride and 2 cc of anhydrous pyridine. The mixture is shaken for 4 days at a temperature in the vicinity of 20° C. After the mixture has been evaporated to dryness, the residue is chromatographed on a silica plate (Merck 60 F254; methylene chloride/methanol 95:5 by volume). A compound (8 mg) is isolated, the characteristics of which are as follows:

Rf=0.60 proton nuclear magnetic resonance spectrum (200 MHz, dissolved in CD4O):

| | |
|---|---|
| CO—C—H$_3$ | $\delta_H$ = 1.90 and 2.16 ppm (2s) |
| —C(3)-H | $\delta_H$ = 6.14 ppm (d, J = 7.5 Hz) |
| =C(5')-H | $\delta_H$ = 7.56 ppm (s) |

Between the acetylated and non-acetylated "bis(2,4-dinitrophenyl)" derivatives, there is a difference $\Delta\delta_H$=1.34 ppm, which confirms the presence of a hydroxyl radical in position 3—.

According to a feature of the invention, girolline is obtained by extracting ground and freeze-dried Pseudaxinyssa cantharella with ethanol and/or methanol. The extract is purified by successive chromatography on appropriate media eluting with suitable solvents or solvent mixtures.

The girolline may be isolated in the form of an addition salt with an inorganic or organic acid such as hydrochloric acid.

Girolline has remarkable antitumoral properties. In vitro, it has proved active on P 388 leukemia cells at concentrations of between 0.001 and 1 μg/cc. The activity in vitro has been confirmed in vivo in mice grafted with P 388 leukemia cells at doses in the vicinity of 1 mg/kg, administered intra-peritoneally.

The present invention also provides pharmaceutical compositions which contain girolline in combination with another pharmaceutically acceptable product such as a diluent or adjuvant which may be inert or physiologically active.

These compositions may be presented in any form which is suitable for the administration route required. The parenteral route, and especially the intravenous route, is the preferential route of administration.

The compositions according to the invention for parenteral administration may be aqueous or non-aqueous sterile solutions, suspensions or emulsions. As solvent or vehicle, propylene glycol, vegetable oils, especially olive oil, and injectable organic esters, for example, ethyl oleate, may be employed. These compositions may also include adjuvants, especially, wetting agents, emulsifiers and dispersants. The sterilization may be carried out in several ways, for example, by means of a bacteriological filter, by incorporating sterilizing agents into the composition, by irradiation or by heating. They can also be prepared in the form of sterile solid compositions which may be dissolved or dispersed in sterile water or any other injectable sterile medium at the time of use.

Girolline may be used in the treatment of malignant hemopathies and solid tumors, at a daily dose which is generally between 0.1 and 1 mg/kg, administered intravenously, for an adult.

The following Examples illustrate the invention.

EXAMPLE 1

Frozen Pseudaxinyssa cantharella sponges (25 kg) are ground and freeze-dried. 5 kg of the crude product containing 45% of sodium chloride are extracted with ethanol (3×6.5 liters). The ethanolic phase is concentrated to dryness. 1 kg of the dry extract is taken up with methanol (6 liters). The methanol-soluble fraction is evaporated and taken up with water (10 liters). The water-soluble fraction is dried and taken up with methanol (4 liters). After distilling off the methanol, a pasty extract (477 g) is obtained, which is absorbed on 439 g of silica.

The extract (365 g) absorbed on silica is chromatographed on a column of 8 cm diameter containing 800 g of silica gel (60 Merck 7734 type) eluting with an ethyl acetate:methylethyl ketone:formic acid:water mixture (initially 5:3:0.5:0.5 by volume) in which the proportions of formic acid and water are gradually increased, and collecting 400 cc fractions. Each fraction is monitored by thin layer chromatography, the plates being developed by spraying with sodium hypochlorite solution, followed, after drying, by spraying with a saturated solution of o-tolidine in water acidified with 2% acetic acid. 70 fractions are collected, which are combined into 16 batches. The first eight batches corresponding to the fractions 1 to 36 contain only the products which are less polar than girolline. The tenth batch (containing 25.1 g of solid), which corresponds to five fractions eluted with an ethyl acetate:methylethyl ketone:formic acid:water mixture in the proportions of 5:5:2:2 by volume, has the highest girolline content.

The crude girolline thus obtained is filtered through a 5 cm diameter column containing 800 g of Sephadex LH 20 gel, eluting with methanol. Pure girolline (5.05 g), in a yield of 0.5 g per kg of the frozen sponge, is thus obtained.

EXAMPLE 2

A solution containing girolline (16 mg/cc) is prepared by dissolving 1.6 g of this compound in apyrogenic normal saline in a quantity sufficient to produce 100 cc. The solution is distributed aseptically into ampoules at a rate of 5 cc per ampoule. The ampoules are sealed; they each contain 80 mg of girolline.

We claim:

1. Girolline of the formula:

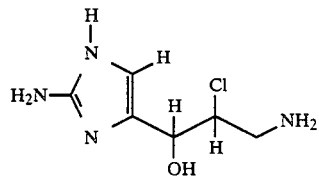

and its pharmaceutically acceptable acid addition salts.

2. A process for the preparation of girolline as claimed in claim 1, which comprises extracting ground, freeze-dried Pseudaxinyssa cantharella sponge with an alcohol selected from the class consisting of ethanol and methanol, and purifying the extract by chromatography.

3. Process according to claim 4 in which the product obtained is converted into a pharmaceutically acceptable acid addition salt.

4. A pharmaceutical composition useful as an anti-tumor agent comprising an anti-tumor effective amount of girolline as claimed in claim 1 or a pharmaceutically acceptable acid addition salt thereof, in combination with a pharmaceutically acceptable diluent or adjuvant.

* * * * *